US 6,605,438 B1

(12) United States Patent
Dischler

(10) Patent No.: US 6,605,438 B1
(45) Date of Patent: Aug. 12, 2003

(54) LYOPHILIZING OF LIQUID DROPS HAVING ARBITRARY EDGES AND APPLICATION THEREOF TO MICROARRAYS OF BIOLOGICAL REAGENTS

(76) Inventor: Louis Dischler, 252 W. Park Dr., Duncan Park, Spartanburg, SC (US) 29306-5013

( * ) Notice: Subject to any disclaimer, the term of this patent is extended or adjusted under 35 U.S.C. 154(b) by 49 days.

(21) Appl. No.: 09/817,652

(22) Filed: Mar. 26, 2001

(51) Int. Cl.[7] .............................. C12Q 1/68; C12M 1/36; G01N 15/06; C07H 21/02; C12N 9/00
(52) U.S. Cl. .......................... 435/6; 435/7.1; 435/174; 435/283.1; 435/287.2; 422/50; 422/58; 422/68.1; 422/101; 436/518; 530/300; 530/350; 536/23.1
(58) Field of Search .................. 435/6, 174, 287.2, 435/283.1, 7.1; 530/300, 350; 536/23.1; 422/68.1, 50, 58, 101; 436/518

(56) References Cited

U.S. PATENT DOCUMENTS

| | | | | |
|---|---|---|---|---|
| 5,192,503 A | * | 3/1993 | McGrath et al. | 422/57 |
| 5,727,333 A | * | 3/1998 | Folan | |
| 5,807,522 A | * | 9/1998 | Brown et al. | 422/50 |
| 2001/0049148 A1 | * | 12/2001 | Wolk et al. | 436/180 |

OTHER PUBLICATIONS

Merriam–Webster's Collegiate Thesaurus (www.search.eb.com/thesaurus?hdws=arbitrary&book=dictionary&swap=thes.*
Merriam–Webster's Collegiate Thesaurus (www.search.eb.com/thesaurus?book=thesaurus&va=ran.*

* cited by examiner

Primary Examiner—B. J. Forman

(57) ABSTRACT

The disclosure relates to the stabilization of a fluid drop comprising a liquid solvent and solute, so that upon drying of the solvent, the solute is not preferentially concentrated at the edges of the residual spot, and more particularly relates to the preparation of microarrays containing biological reagents.

14 Claims, 2 Drawing Sheets

LYOPHILIZING OF LIQUID DROPS HAVING ARBITRARY EDGES AND APPLICATION THEREOF TO MICROARRAYS OF BIOLOGICAL REAGENTS

FIELD OF THE INVENTION

The present invention generally relates to the stabilization of a drop of liquid comprising a solvent and solute, so that upon drying of the solvent to form a spot, the solute is not preferentially concentrated at the edges of the residual spot, and more particularly relates to the preparation of microarrays of spots containing biological reagents.

BACKGROUND OF THE INVENTION

It is a common procedure to prepare arrays of small areas (i.e., spots) of biological reagents on a surface. Generally the biological reagent is dissolved or suspended in a solvent, and a small drop thereof is applied to a prepared surface along with other drops containing other reagents or reagent concentrations to form an array. The array is then dried to remove the solvent, leaving spots of probe reagents. A dried spot is typically not uniform, but dries to form a ring, with the reagent concentrated at the spot edge and almost absent from the center of the spot. This concentration gradient is undesirable, as it reduces the readability of the spots, and degrades measurements thereof. It would therefore be advantageous to provide a spot with a concentration gradient that is more uniform.

SUMMARY OF THE INVENTION

The present invention provides an array of spots containing reagents prepared by lyophilization of drops of liquid comprising a solvent and varying dissolved, dispersed, or emulsified solutes, with an improved concentration gradient of the remaining solute within individual spots after removal of the solvent. Microarrays of biological reagents are often created by applying fluid drops of solvent/solute to a frosted or smooth substrate surface of glass, metal or polymer, and allowing the solvent to evaporate. The substrate is often pre-coated (e.g., with poly-L-lysine or aminosilane) to insure that the reagent adequately adheres to the substrate. Drops of liquid (solvent/solute) applied to the surface typically have a random edge, which is herein defined as the line of contact on a substantially flat portion of the substrate where gas (generally air), substrate, and liquid meet. By "substantially flat", it is meant that there is no ledge or other constraining substrate geometry directly abutting or constraining the random edge.

The fluid drop is typically characterized by, a random edge which is pinned to the surface, that is, as the solvent contained within the drop evaporates from the entire liquid/gas interface, the edge does not substantially retreat as liquid flows in from the central region of the drop to replenish that which has been lost by evaporation at or near the pinned random edge. Drying of the drop during formation of the spot thus involves a continuous transport of solvent and solute outwards towards the pinned random edge, ultimately resulting in the dilution or even complete disappearance of solute in the center of the resultant spot, and the concomitant excess concentration at the location of the pinned random edge. Such an effect may be commonly observed when drops of coffee dry on a saucer or countertop. It is a robust phenomenon, little affected by choice of solvent or solute.

In the present invention, it has been found that this undesired concentration gradient can be eliminated by first freezing the fluid drops before substantial evaporation has occurred, and then subliming the solvent. In this lyophilizing process, the reagent is substantially immobilized, and the final concentration gradient of the spot substantially mirrors the thickness of the drop at the time of freezing. If the spot is hemispherical, the concentration will be greatest at the spot center, while if the spot is substantially flat, the concentration gradient will also be substantially flat.

Freezing of the entire array may be accomplished after the array is prepared. Alternatively, the substrate may be pre-cooled so that freezing occurs during or shortly after deposition of the spots. The solvent may comprise water, alcohols, hydrocarbons, or any other solvent compatible with the solute, but is preferably water. The solute may be liquid and/or solid, and may comprise, for example, nucleic acids such as RNA, DNA and cDNA, amino acids and proteins, salts, denaturing buffers, and cryoprotectants such as carbohydrates or sugars. The array may alternatively comprise a growth medium such as agar on a slide or petri dish substrate, with individual spots comprising varying levels of nutrients, mutagens, or other reagents. When drops comprising nutrients such as amino acids are spotted and later plated with bacteria, various forms of auxotrophs may be distinguished; and similarly, the effects of mutagens and other reagents on bacteria may be compactly and conveniently assessed on one slide, dish, or other suitable substrate.

A second liquid drop may be placed upon a first frozen or lyophilized drop, with the second drop having the same or different solvent and/or solute. The areal concentration may be built up with a number of drops sequentially placed on top of previously frozen or lyophilized drops, and a spot having chemically distinct lamina may be created. Such a layered spot would be useful for storage of spots wherein the reagents in different layers would otherwise react prematurely if applied from a common solute. Similarly, a film may be applied over an array of lyophilized drops, e.g., for protection. A lyophilized array may be kept frozen for extended shelf life, and may be sealed in an inert atmosphere, e.g. argon or nitrogen.

While spots have been described that are substantially circular, they may in fact be of any size or shape without departing from the scope of the invention.

It is an object of at least one embodiment of the present invention, therefore, to provide a method to modify or eliminate undesirable reagent concentration gradients within spots by lyophilizing of liquid drops having pinned edges.

It is another object of at least one embodiment of the invention to provide a method of drying a fluid drop comprising a solvent and solute on a substrate without forming a ring substantially enriched in solute.

It is another object of at least one embodiment of the invention to provide a method for creating a dried spot of reagent on a substrate having a center reagent concentration that is equal to or greater than the reagent concentration at the spot edge.

BRIEF DESCRIPTION OF THE DRAWINGS

The above as well as other objects of the invention will become more apparent from the following detailed description of the preferred embodiments of the invention, when taken together with the accompanying drawings in which.

DETAILED DESCRIPTION OF THE PRESENTLY PREFERRED EMBODIMENTS

Figure 1:
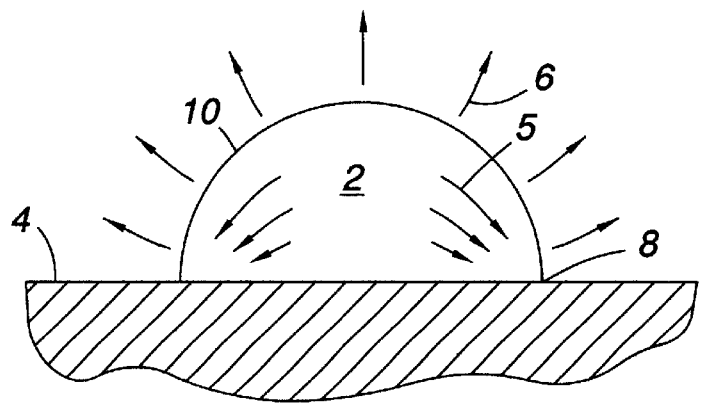
FIG. 1 is a schematic sectional view of a single fluid drop undergoing evaporation.

Referring now to the drawings wherein like numerals refer to like parts, FIG. 1 illustrates a single fluid drop 2 having a substantially hemispherical gas/liquid surface 10. Evaporation occurs in directions 6 from surface 10, resulting in a diminishing thickness of the drop 2. The ratio of the evaporative loss rate of liquid from the drop 2 in relation to its thickness increases without limit from the center of the drop to the drop edge 8—the substrate 4, fluid drop 2, gas interface. Typically this edge 8 is pinned, and liquid within the drop 2 is driven by surface tension in the direction given by arrows 5 towards the pinned drop edge 8, thereby concentrating any solute dispersed or dissolved in or on the drop 2 in the area immediately adjacent to edge 8.

Figure 2:
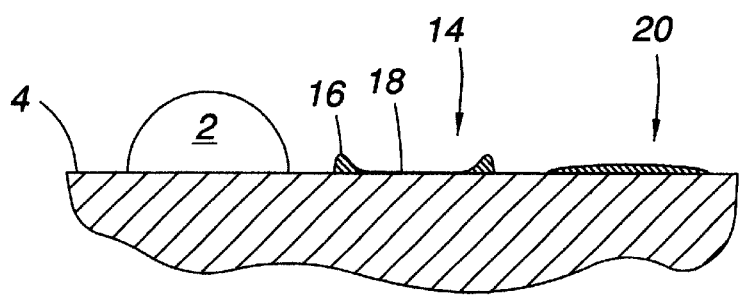
FIG. 2 is a schematic sectional view of two alternative spots derived from a fluid drop by evaporation or lyophilization.

In FIG. 2, two spots 14, 20 are shown that might be derived from drop 2 resting on substrate 4. In the usual case, as in the prior art, spot 14 has been evaporated so that solute contained within the original drop 2 has concentrated into a ring 16 leaving a substantially starved central area 18. By first immobilizing the liquid of drop 2 by freezing, then subliming all or the major portion thereof, little movement of the residual solute results, and a spot 20 having a concentration gradient across spot 20 that mirrors the thickness of the parent drop 2 results, i.e., the concentration is greatest in the center of spot 20 and tapers to the edges.

Figure 3:
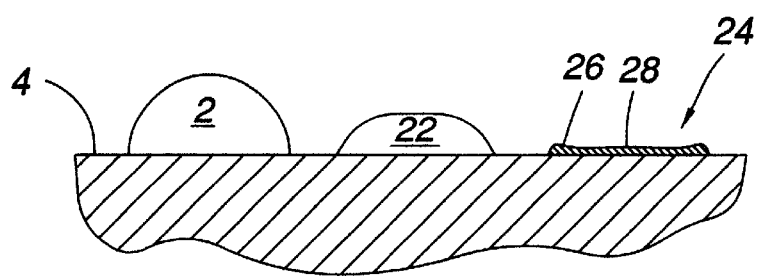
FIG. 3 is a schematic sectional view of three stages of a single fluid drop undergoing evaporation and then lyophilization.

In FIG. 3, three stages of the development of a spot are shown. Original drop 2 is substantially hemispherical, and is allowed to partially evaporate so to form drop 22 having a non-uniform concentration gradient, i.e., the concentration of solute has been concentrated at the drop edge. Drop 22 is the lyophilized to form spot 24, which has a undulating concentration gradient having local maxima at the drop center 28 and near the spot edge 26, but which exhibits on average a more uniform concentration across the width of the spot that that exhibited by lyophilized spot 20 of FIG. 2.

Figure 4:
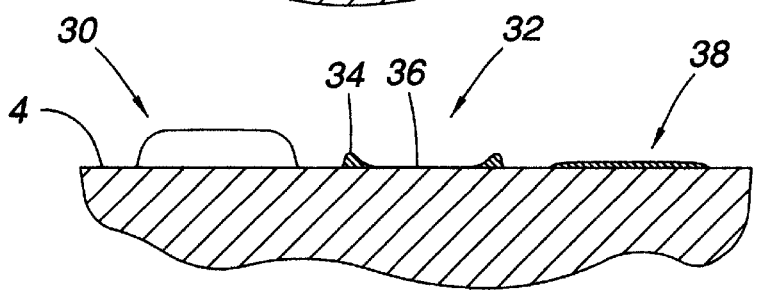
FIG. 4 is a schematic sectional view of two alternative spots derived from a fluid drop by evaporation or lyophilization.

In FIG. 4, the starting drop 30 has flatter geometry compared to the hemispherical drops previously discussed. Upon evaporation, however, a spot 32 according to the prior art is produced that has a pronounced ring concentration along the spot edge 34, while the central region 36 has a much lower concentration of solute. By lyophilizing drop 30 to from spot 38, according to the present invention, a concentration gradient of residual solute is formed that essentially reflects the original thickness of the drop 30 just prior to freezing, i.e., it is uniform except for the area very near the spot edge.

Figure 5:
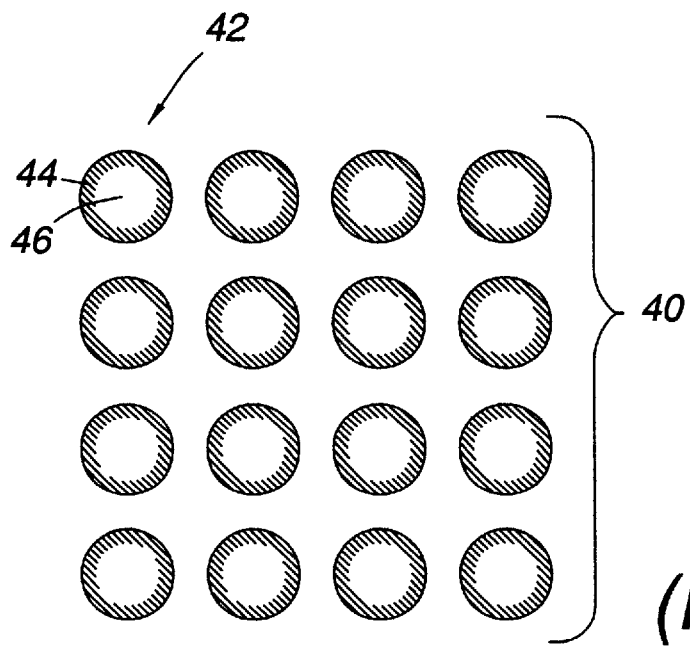
FIG. 5 is a schematic top view of an array of spots evaporated from drops.
Figure 6:
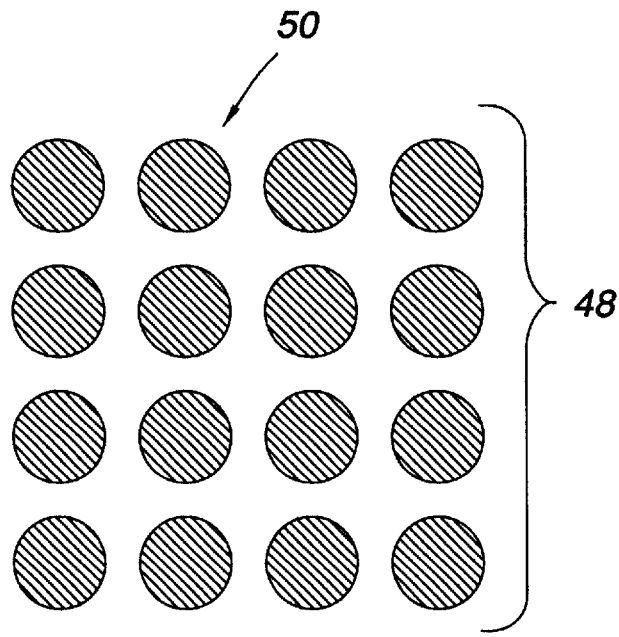
FIG. 6 is a schematic top view of an array of spots lyophilized from drops.

An array of spots 40 formed by the evaporation of drops is shown in FIG. 5, as would be produced by the prior art. Solute originally contained with the drops has been transported and deposited into the ring area 44, leaving the central region 46 of each spot 42 with a low relative concentration of solute. In FIG. 6, a similar array of spots 48 have been formed from drops by lyophilization according to the present invention, thereby producing spots 50 without central voids.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means-plus-function clauses are intended to cover the structures described herein as performing the recited function and not only structural equivalents, but also equivalent structures.

I claim:

1. A method of preparing spots on a substrate surface, comprising the steps of:
   (a) providing a first fluid liquid drop comprising a random edge in contact with a substantially flat portion of the substrate surface, wherein said first fluid liquid drop comprises a first solvent liquid and a first solute;
   (b) cooling the substrate surface prior to step "a", so that said first solvent liquid is frozen by contact with the cooled substrate surface; and
   (c) subsequently subliming substantially all of said first solvent liquid to form a first spot comprising a first concentration gradient of said first solute, wherein said first concentration gradient is substantially unmodified by evaporation of said first solvent liquid from said first fluid liquid drop.

2. A method of preparing spots on a substrate surface, as recited in claim 1, further comprising the step of:
   prior to step "c", providing at least a second fluid liquid drop comprising a random edge in contact with a substantially flat portion of the substrate surface, wherein said second fluid liquid drop comprises a second solvent liquid and a second solute, and wherein said second solvent liquid is frozen by contact with the cooled substrate surface.

3. A method of preparing spots on a substrate surface, as recited in claim 2, wherein said second solute is different from said first solute.

4. A method of preparing spots on a substrate surface, as recited in claim 2, wherein said second solvent liquid is different from said first solvent liquid.

5. A method of preparing spots on a substrate surface, as recited in claim 4, wherein said second solute is different from said first solute.

6. A method of preparing spots on a substrate surface, as recited in claim 1, wherein said first solute is a dissolved solid.

7. A method of preparing spots on a substrate surface, as recited in claim 1, wherein said first solute is an amino acid.

8. A method of preparing spots on a substrate surface, as recited in claim 1, wherein said first solute comprises a nucleic acid.

9. A method of preparing spots on a substrate surface, as recited in claim 8, wherein said nucleic acid is cDNA.

10. A method of preparing spots on a substrate surface, as recited in claim 1, wherein said solute is a liquid.

11. A method of preparing spots on a substrate surface, as recited in claim 1, wherein said first solvent liquid is water.

12. A method of preparing spots on a substrate surface, as recited in claim 1, wherein said first solute is dispersed in said first solvent liquid.

13. A method of preparing spots on a substrate surface, as recited in claim 1, further comprising, after said subliming substantially all of said first solvent liquid, the steps of:
   (d) subsequent to freezing said first fluid drop, providing a second fluid drop comprising a second liquid solvent and a second solute so as to at least partially cover the first drop or spot;

(e) cooling the substrate surface prior to step "d", so that said second fluid drop is frozen by contact with the cooled substrate surface; and (f) subsequently subliming substantially all of said second liquid.

14. A method of preparing an array of dried spots of solute on a substrate surface, comprising the steps of:

(a) providing an array of spaced fluid drops on the substrate surface, wherein each of said spaced fluid drops comprises a solvent liquid and a variable solute, and a random edge in contact with a substantially flat portion of the substrate surface, and wherein said random edge of each of said spaced fluid drops is not coincident with any raised surface geometry on the substrate surface;

(b) cooling the substrate surface prior to step "a", so that said array of spaced fluid drops is frozen by contact with the cooled substrate surface; and (c) subsequently subliming substantially all of said first solvent liquid from said array of spaced fluid drops with substantially no evaporation, thereby preparing said array of dried spots.

* * * * *